United States Patent [19]
Limburg et al.

[11] Patent Number: 5,011,939
[45] Date of Patent: Apr. 30, 1991

[54] HYDROXY FUNCTIONALIZED ARYLAMINE COMPOUNDS

[75] Inventors: William W. Limburg, Penfield; John F. Yanus; Dale S. Renfer, both of Webster; Richard L. Schank, Pittsford, all of N.Y.; Beng S. Ong, Mississauga, Canada

[73] Assignee: Xerox Corporation, Stamford, Conn.

[21] Appl. No.: 355,728

[22] Filed: May 23, 1989

Related U.S. Application Data

[60] Division of Ser. No. 198,254, May 24, 1988, which is a continuation-in-part of Ser. No. 61,247, Jun. 10, 1987, abandoned.

[51] Int. Cl.$^5$ .................. C07D 209/82; C07C 211/00; C07C 209/00
[52] U.S. Cl. .................... 548/440; 564/426; 564/427; 564/430; 564/431; 564/434; 564/395
[58] Field of Search ............... 548/440; 564/426, 427, 564/431, 395, 430, 434

[56] References Cited

FOREIGN PATENT DOCUMENTS 2262157 7/1973 Fed. Rep. of Germany .
2473740 1/1981 France .

OTHER PUBLICATIONS

Chemical Abstracts, vol. 70, 1969, 87303t, Triarylamines Substituted in the Ortho Position Frye, Cecil L. Fr., 1, 511, 252, Jan. 26, 1968.
Chemical Abstracts, vol. 73, 1970, 47502, Hydroxy Triphenylamines as Antiozonants for Rubber and Gasoline, Spacht, Ronald B., U.S. Pat. No. 3,508,888, Apr. 28, 1970.

Primary Examiner—Mary C. Lee
Assistant Examiner—Joseph K. McKane
Attorney, Agent, or Firm—Peter H. Kondo

[57] ABSTRACT

A hydroxy arylamine compound is disclosed represented by the formula:

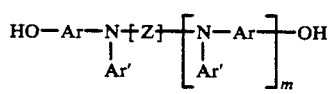

wherein:
m is 0 or 1,
Z is selected from the group consisting of:

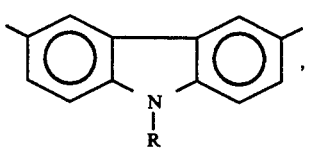

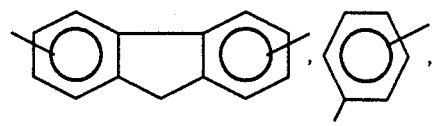

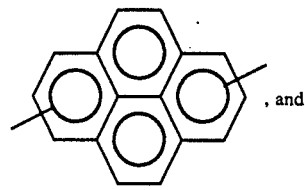

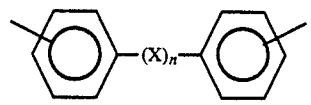

n is 0 or 1,
Ar is selected from the group consisting of:

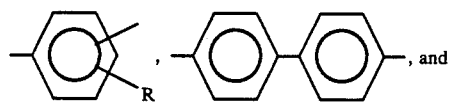

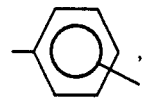

R is selected from the group consisting of —CH$_3$, —CH$_2$H$_5$, —C$_3$H$_7$, and —C$_4$H$_9$,
Ar' is selected from the group consisting of:

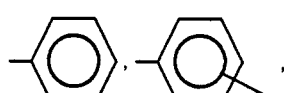

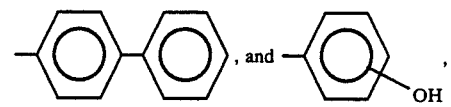

X is selected from the group consisting of:

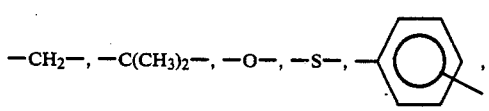

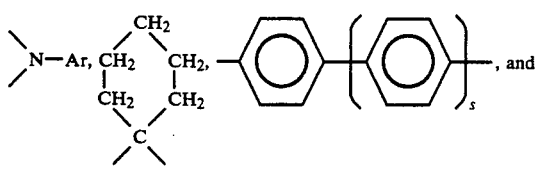

(Abstract continued on next page.)

-continued
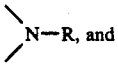
s is 0, 1 or 2,
the dihydroxy arylamine compound being free of any direct conjugation between the —OH groups and the nearest nitrogen atom through one or more aromatic rings. The dihydroxy arylamine compound may be employed in an electrophotographic imaging member and the member may be used in an electrophotographic imaging process.
3 Claims, No Drawings

HYDROXY FUNCTIONALIZED ARYLAMINE COMPOUNDS

This application is a divisional application of copending application Ser. No. 07/198,254, filed May 24, 1988 now U.S. Pat. No. 4,871,634. The entire disclosure of copending application Ser. No. 07/198,254 is incorporated herein by reference. Application Ser. No. 07/198,254 is a continuation-in-part aplication of application Ser. No. 07/061,247, filed June 10, 1987, now abandoned. The entire disclosure of application Ser. No. 07/061,247 is incorporated herein by reference.

BACKGROUND OF THE INVENTION

This invention relates in general to arylamine compounds and more specifically, to hydroxy arylamine compounds and electrophotographic imaging members and processes utilizing such hydroxy arylamine compounds.

In the art electrophotography an electrophotographic plate comprising a photoconductive insulating layer on a conductive layer is imaged by first uniformly electrostatically charging the surface of the photoconductive insulating layer. The plate is then exposed to a pattern of activating electromagnetic radiation such as light, which selectively dissipates the charge in the illuminated areas of the photoconductive insulating layer while leaving behind an electrostatic latent image in the non-illuminated areas. This electrostatic latent image may then be developed to form a visible image by depositing finely divided electroscopic toner particles on the surface of the photoconductive insulating layer. The resulting visible toner image can be transferred to a suitable receiving member such as paper. This imaging process may be repeated many times with reusable photoconductive insulating layers.

As more advanced, higher speed electrophotographic copiers, duplicators and printers were developed, degradation of image quality was encountered during cycling. Moreover, complex, highly sophisticated, duplicating and printing systems operating at high speeds have placed stringent requirements including narrow operating limits on photoreceptors. For example, the numerous layers found in many modern photoconductive imaging members must be highly flexible, adhere well to to adjacent layers, and exhibit predictable electrical characteristics within narrow operating limits to provide excellent toner images over many thousands of cycles. There is also a great current need for long service life, flexible photoreceptors in compact imaging machines that employ small diameter support rollers for photoreceptor belt systems compressed into a very confined space. Small diameter support rollers are also highly desirable for simple, reliable copy paper stripping systems which utilize the beam strength of the copy paper to automatically remove copy paper sheets from the surface of a photoreceptor belt after toner image transfer. However, small diameter rollers, e.g. less than about 0.75 inch (19 mm) diameter, raise the threshold of mechanical performance criteria for photoreceptors to such a high level that spontaneous photoreceptor belt material failure becomes a frequent event for flexible belt photoreceptors.

One type of multilayered photoreceptor that has been employed as a belt in electrophotographic imaging systems comprises a substrate, a conductive layer, a charge blocking layer a charge generating layer, and a charge transport layer. The charge transport layer often comprises an activating small molecule dispersed or dissolved in an polymeric film forming binder. Generally, the polymeric film forming binder in the tranport layer is electrically inactive by itself and becomes electrically active when it contains the activating molecule. The expression "electrically active" means that the material is capable of supporting the injection of photogenerated charge carriers from the material in the charge generating layer and is capable of allowing the transport of these charge carriers through the electrically active layer in order to discharge a surface charge on the active layer. The multilayered type of photoreceptor may also comprise additional layers such as an anti-curl backing layer, an adhesive layer, and an overcoating layer. Although excellent toner images may be obtained with multilayered belt photoreceptors that are developed with dry developer powder (toner), it has been found that these same photoreceptors become unstable when employed with liquid development systems. These photoreceptors suffer from cracking, crazing, crystallization of active compounds, phase separation of activating compounds and extraction of activating compounds caused by contact with the organic carrier fluid, isoparaffinic hydrocarbons e.g. Isopar, commonly employed in liquid developer inks which, in turn, markedly degrade the mechanical integrity and electrical properties of the photoreceptor. More specifically, the organic carrier fluid of a liquid developer tends to leach out activating small molecules, such as the arylamine containing compounds typically used in the charge transport layers. Representative of this class of materials are: N,N'-diphenyl-N,N'-bis(3-methylphenyl)-[1,1'-biphenyl]-4,4'-diamine; bis-(4-diethylamino-2-methylphenyl)-phenylmethane; 2,5-bis-(4'-dimethylaminophenyl)-1,3,4,-oxadiazole; 1-phenyl-3-(4'-diethylaminostryryl)-5-(4''-diethylaminophenyl)-pyrazoline; 1,1-bis-(4'-p-(di-N,N'-p-methylphenyl)-aminophenyl)-cyclohexane; 4-diethylaminobenzaldehyde-1,1-diphenylhydrazone; 1,1-diphenyl-2(p-N,N-diphenyl amino phenyl)-ethylene; N-ethylcarbazole-3-carboxaldehyde-1-methyl-1-phenylhydrazone. The leaching process results in crystallization of the activating small molecules, such as the aforementioned arylamine compounds, onto the photoreceptor surface and subsequent migration of arylamines into the liquid developer ink. In addition, the ink vehicle, typically a C10–C14 branches hydrocarbon, induces the formation of cracks and crazes in the photoreceptor surface. These effects lead to copy defects and shortened photoreceptor life. The degradation of the photoreceptor manifests itself as increased background and other printing defects prior to complete physical photoreceptor failure. The leaching out of the activating small molecule also increases the susceptibility of the transport layer to solvent/stress cracking when the belt is parked over a belt support roller during periods of non-use. Some carrier fluids may also promote phase separation of the activating small molecules, such as arylamine compounds, in the transport layers, particularly when high concentrations of the arylamine compounds are present in the transport layer binder. Phase separation of activating small molecules also adversely alters the electrical and mechanical properties of a photoreceptor. Similarly, single layer photoreceptors having a single active layer comprising photoconductive particles dispersed in a charge transport film forming binder are also vulnerable to the same degradation problems encountered by the previously described multilayered type of photoreceptor when exposed to liquid developers. Although flexing is normally not encountered with rigid, cylindrical, multilayered photoreceptors which utilize charge transport layers containing activating small molecules dispersed or dissolved in a polymeric film forming binder, electrical degradation are similarly encountered during development with liquid developers. Sufficient degradation of these photoreceptors by liquid developers can occur in less than two hours as indicated by leaching of the small molecule and cracking of the matrix polymer film. Continued exposure for several days severely damages the photoreceptor.

Photoreceptors have been developed which comprise charge transfer complexes prepared with polymeric molecules. For example, charge transfer complexes formed with polyvinyl carbazole are disclosed in U.S. Pat. Nos. 4,047,948, 4,346,158 and 4,388,392. Photoreceptors utilizing polyvinyl carbazole layers, as compared with current photoreceptor requirements, exhibit relatively poor xerographic performance in both electrical and mechanical properties. Polymeric arylamine molecules prepared from the condensation or di-secondary amine with a di-iodo aryl compound are disclosed in European patent publication No. 34,425, published Aug. 26, 1981, issued May 16, 1984. Since these polymers are extremely brittle and form films which are very susceptable to physical damage, their use in a flexible belt configuration is precluded. Thus, in advanced imaging systems utilizing multilayered belt photoreceptors exposed to liquid developement systems, cracking and crazing have been encountered in critical charge transport layers during belt cycling. Cracks developing in charge transport layers during cycling can be manifested as print-out defects adversely affecting copy quality. Furthermore, cracks in the photoreceptor pick up toner particles which cannot be removed in the cleaning step and may be transferred to the background in subsequent prints. In addition, crack areas are subject to delamination when contacted with blade cleaning devices thus limiting the options in electrophotographic product design.

Photoreceptors having charge transport layers containing small molecule arylamine containing compounds dispersed or dissolved in various resins such as polycarbonates are known in the art. Similarly, photoreceptors utilizing polymeric arylamine containing molecules such as polyvinyl carbazole, polymethacrylates possessing pendant arylamines are also known. Further, condensation polymers of a di-secondary amine with a di-iodo aryl compound are described in the prior art.

PRIOR ART STATEMENT

U.S. Pat. No. 3,658,520 to Brantley et al, issued Apr. 25, 1972—A photoconductive composition is disclosed comprising a triarylamine wherein at least one of the aryl radicals is substituted by an active hydrogen-containing group and a sensitizer for the photoconductor. Typical active hydrogen-containing groups which are substituted on an aryl radical include hydroxy radicals. See for example, column 2, lines 4, 5 and 19.

U.S. Pat. No. 4,539,282 to Morimoto et al, issued Sept. 3, 1985—An electrophotographic photosensitive element is disclosed containing zinc oxide in combination with a polycarbonate binder and a compound which contains hydroxyl groups substituted in phenylene rings in the molecule. See for example, column 4, lines 38 and 39.

Japanese Patent Publication No. J5 8002-849 to Konishiroku, published Jan. 8, 1983—An electrophotographic photoreceptor is disclosed comprising a carrier generation layer and a carrier transport layer. The carrier transport layer contains (a) an amine derivative having optional substituted aromatic hydrocarbon or optional substituted aromatic heterocyclic groups attached to the nitrogen atom (e.g. see page 4, column 14, compound A-4); (b) a carbazole derivative; and (c) a polymeric organic semiconductor having a condensed aromatic ring or hetero ring in the side chain.

U.S. Pat. No. 4,395,475 to Noonan et al, issued July 26, 1983—Polymeric photoconductors are disclosed comprising a condensation polymer backbone containing, as repeating units, the condensation residues of (1) a dicacid and (2) an organic difunctional compound capable of undergoing condensation polymerization with the diacid, and an arylamine photoconductor group appended to at least one of the acid or organic difunctional compound residues.

Japanese Patent Publication No. J5 8099-447-A to Daicel Chem Ind KK, published June 13, 1983—A charge-transfer complex of N,N,N',N'-tetrakis-(p-substituted phenyl)-p-phenylene diamine and iodine is disclosed. This material can be used in a photoelectric element or a photoconductive element.

U.S. Pat. No. 4,587,189 to Hor et al, issued May 6, 1986—A layered photoresponsive imaging member is disclosed comprising a substrate; a vacuum evaporated photogenerator layer comprising a perylene pigment; and an arylamine hole transport layer comprising a diamine.

Canadian Pat. No. 1,171,431 (corresponding to European Patent Application No. 34,425 to Xerox, published Aug. 26, 1981, issued May 16, 1984)—Condensation polymers of a di-secondary amine with a di-iodoaryl are described, for example, in working Examples IX and X.

U.S. Pat. No. 4,052,205 to Stolka et al, issued Oct. 4, 1977—A photoconductive imaging member is disclosed comprising various active polymers, such as poly-N-vinyl carbazole, in a transport layer, e.g. line 45, column 5 to line 27, column 6. Derivatives of the active polymers may be hydroxy substituted, e.g. column 5, lines 62–65.

U.S. Pat. No. 4,415,641 to Goto et al, issued Nov. 15, 1983—An electrophotographic light-sensitive element is disclosed comprising a carbazole derivative (see column 3, lines 1–14). $R_2$ can represent a hydroxy group.

Stolka et al, Photoconductivity and Hole Transport in Polymers of Aromatic Amine-Containing Methacrylates, Journal of Polymer Science. Polymer Chemistry Edition, Vol. 21, 969 (1983)—Hole transport is described in high molecular weight arylamine-substituted polymethacrylates. Synthesis of the monomers, their polymerization, and the general properties of these polymers are also discussed.

U.S. Pat. No. 3,844,781 to Tsuchiya et al, issued Oct. 29, 1974— Various photoconductive materials are disclosed containing substituents such as hydroxyl, amino and alkoxy groups.

U.S. Pat. No. 3,890,146 to Nagashima et al, issued June 17, 1975—Various photoconductive materials are disclosed containing substituents such as hydroxyl, amino and alkoxy groups.

U.S. Pat. No. 4,588,666 to Stolka et al, issued May 13, 1986—A hole transporting molecule is disclosed comprising alkoxy derivatives of tetra phenyl biphenyl diamine (see column 3, lines 33–66). $R_1$ and $R_2$ represent alkoxy groups which include methoxy. Resins such as polyvinyl carbazoles, polycarbonate resins, epoxy resins, polyvinyl butyrals, polyhydroxyether resins may be sued as a binder fro the hole transporting molecule.

U.S. Pat. No. 4,265,990 to Stolka et al, issued May 5, 1981—Transport layers are disclosed comprising small molecule arylamines and a polycarbonate resin binder.

U.S. Pat. No. 4,047,948 to A. M. Horgan, issued Sept. 13, 1977—A photoreceptor is disclosed comprising layers which may contain polyvinyl carbazole. The use of small molecule arylamine activating compounds in transport layers is also disclosed. The preferred small molecule resin binder is a polycarbonate resin.

U.S. Pat. No. 4,346,158 to Pai et al, issued Aug. 24, 1982—A photoreceptor is disclosed comprising layers which may contain polyvinyl carbazole. The use of small molecule arylamine activating compounds in transport layers is also disclosed. The preferred small molecule resin binder is a polycarbonate resin.

U.S. Pat. No. 4,588,667 to Jones, issued May 13, 1986—Various overcoated electrophotographic imaging members are disclosed including a multilayered imaging member having a substrate, a titanium metal layer, a siloxane blocking layer, an adhesive layer, a charge generating binder layer, and a charge transport layer. The transport layer may contain from about 25 to about 75 percent by weight of arylamine transport material in a resin binder such as polycarbonate resin.

U.S. Pat. No. 4,388,392 to Kato et al, issued June 14, 1987, A photoreceptor is disclosed comprising layers which may contain polyvinyl carbazole. The use of an electron-donative polycyclic aromatic hydrocarbon incorporated in an electro-donative polymeric photoconductor in a charge transporting layer is also disclosed.

U.S. Pat. No. 4,273,846 to Pai et al, issued June 16, 1981 An imaging member is disclosed comprising a polycarbonate resin material and an arylamine (see the general formula, column 2, lines 21-34). Poly-N-vinyl carbazole may be employed in the generator layer.

Thus, there is a continuing need for multilayered photoreceptors having improved resistance to cracking, crazing, crystallization of active compounds, phase separation of active compounds and leaching of active compounds.

SUMMARY OF THE INVENTION

It is, therefore, an object of the present invention to provide an improved aryl amine compound for a photoresponsive member which overcomes the above-noted disadvantages.

It is yet another object of the present invention to provide an improved aryl amine containing electrophotographic member which exhibits greater resistance to cracking and crazing upon exposure to liquid development systems.

It is a further object of the present invention to provide a photoconductive imaging member which exhibits improved resistance to component leaching during liquid development.

It is still another object of the present invention to provide a photoconductive imaging member which exhibits improved resistance to component crystallization during liquid development.

It is a further object of the present invention to provide an electrophotographic imaging member which retains stable electrical properties during cycling.

The foregoing objects and others are accomplished in accordance with this invention by providing a hydroxy arylamine compound represented by the formula:

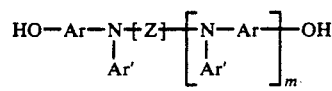

wherein:
m is 0 or 1,
Z is selected from the group consisting of:

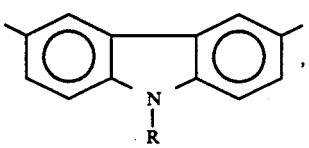

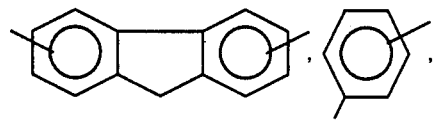

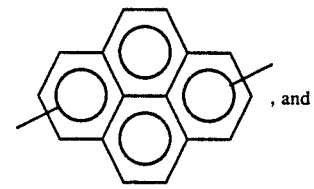

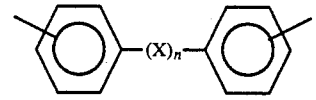

n is 0 or 1,
Ar is selected from the group consisting of:

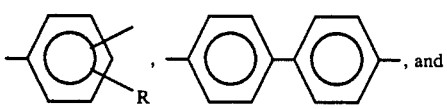

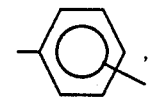

R is selected from the group consisting of —CH$_3$, —C$_2$H$_5$, —C$_3$H$_7$, and —C$_4$H$_9$,
Ar' is selected from the group consisting of:

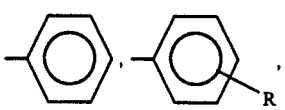

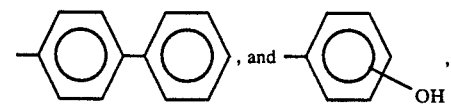

X is selected from the group consisting of:

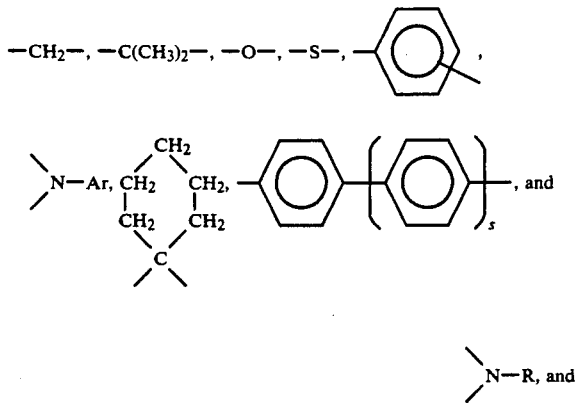

s is 0, 1 or 2,
the dihydroxy arylamine compound being free of any direct conjugation between the —OH groups and the nearest nitrogen atom through one or more aromatic rings.

The expression "direct conjugation" is defined as the presence of a segment having the formula:

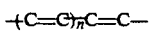

where n=0 or 1 in one or more aromatic rings directly between an —OH group and the nearest nitrogen atom. Examples of direct conjugation between the —OH groups and the nearest nitrogen atom through one or more aromatic rings include a compound containing a phenylene group having an —OH group in the ortho or para position (or 2 or 4 position) on the phenylene group relative to a nitrogen atom attached to the phenylene group or a compound containing a polyphenylene group having an —OH group in the ortho or para position on the terminal phenylene group relative to a nitrogen atom attached to an associated phenylene group.

The following two structures are illustrative examples of specific compounds in which the hydroxyl group is in direct conjugation with the nitrogen through a phenylene ring system.

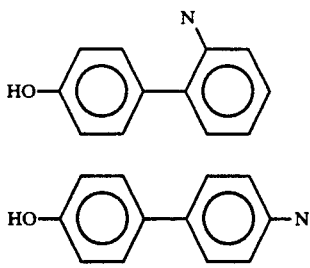

The hydroxy arylamine compound of this invention is utilized in an electrophotographic imaging member comprising a substrate having an electrically conductive surface, a charge blocking layer, a charge generation layer, and a hole transport layer and at least the charge transport layer or the charg generation layer comprising the above described hydroxy aryl amine bound by hydrogen bonding to a resin capable of hydrogen bonding.

The hydroxy arylamine compound of this invention is also utilized in an electrophotographic imaging member comprising a substrate having an electrically conductive surface, a charge blocking layer and a photogeneration layer, the photogeneration layer comprising photoconductive pigment particles dispersed in the above described hydroxy aryl amine bound by hydrogen bonding to a resin capable of hydrogen bonding.

The hydroxy arylamine compound of this invention is also utilized in an electrophotographic imaging member comprising a substrate having an electrically conductive surface, a charge blocking layer, a charge generation layer, a hole transport layer, and an overcoating layer comprising the hydroxy aryl amine bound by hydrogen bonding to a resin capable of hydrogen bonding.

The electrophotographic imaging member of this invention may be employed in any suitable electrophotographic imaging process.

Generally, the hydroxy arylamine compounds of this invention are prepared, for example, by hydrolyzing an dialkoxy arylamine. A typical process for preparing alkoxy arylamines is disclosed in Example I of U.S. Pat. No. 4,588,666 to Stolka et al, the entire disclosure of this patent being incorporated herein by reference. The dihydroxy arylamine compound of this invention should be free of any direct conjugation between the —OH groups and the nearest nitrogen atom through one or more aromatic rings because layers containing compounds having such direct conjugation fail to support transport of electrical charges.

Typical hydroxy arylamine compounds of this invention include, for example:

N,N'-diphenyl-N,N'-bis(3-hydroxyphenyl)-[1,1'-biphenyl]-4,4'-diamine;
N,N,N',N',-tetra(3-hydroxyphenyl)-[1,1'-biphenyl]-4,4'-diamine;
N,N-di(3-hydroxyphenyl)-m-toluidine;
1,1-bis-[4-(di-N,N-m-hydroxpyphenyl)-aminophenyl]-cyclohexane;
1,1-bis[4-(N-m-hydroxyphenyl)-4-(N-phenyl)-aminophenyl]-cyclohexane;
Bis-(N-(3-hydroxyphenyl)-N-phenyl-4-aminophenyl)-methane;
Bis[(N-(3-hydroxyphenyl)-N-phenyl)-4-aminophenyl]-isopropylidene;
N,N'-diphenyl-N,N'-bis(3-hydroxyphenyl)-[1,1':4',1''-terphenyl]-4,4''-diamine;
9-ethyl-3.6-bis[N-phenyl-N-3(3-hydroxyphenyl)-amino]-carbazole;
2,7-bis[N,N-di(3-hydroxyphenyl)-amino]-fluorene;
1,6-bis[N,N-di(3-hydroxyphenyl)-amino]-pyrene;
1,4-bis[N-phenyl-N-(3-hydroxyphenyl)]-phenylenediamine.

Typical hydroxy arylamine compounds containing direct conjugation between the —OH groups and the nearest nitrogen atom through one or more aromatic rings include, for example:

N,N'-diphenyl-N-N'-bis(4-hydroxyphenyl)[1,1'-biphenyl]-4,4'-diamine;
N,N,N',N',-tetra(4-hydroxyphenyl)-[1,1'-biphenyl]-4,4'-diamine;
N,N-di(4-hydroxyphenyl)-m-toluidine;
1,1-bis-[4-(di-N,N-p-hydroxpyphenyl)-aminophenyl]-cyclohexane;
1,1-bis[4(N-o-hydroxyphenyl)-4-(N-phenyl)-aminophenyl]-cyclohexane;

Bis-(N-(N4-hydroxyphenyl)-N-phenyl-4-aminophenyl)-methane;
Bis[(N-(4-hydroxyphenyl)-N-phenyl-4-aminophenyl]-isopropylidene;
Bis-N,N-[(N4'-hydroxy-4-(1,1'-biphenyl)]-aniline
Bis-N,N-[(2'-hydroxy-4(1,1'-biphenyl)]-aniline A photoconductive imaging member of this invention may be prepared by providing a substrate having an electrically conductive surface, applying a charge blocking layer on the electrically conductive surface, applying a charge generation layer on the blocking layer and applying a charge transport layer on the charge generation layer. If desired, the charge transport layer may be applied to the electrically conductive surface and the charge generation layer may thereafter be applied to the charge transport layer. The hydroxy aryl amine of this invention bound by hydrogen bonding to a resin capable of hydrogen bonding may be incorporated into the charge generation layer, charge transport layer, or protective overcoating.

Any suitable polar resin capable of hydrogen bonding with the hydroxy aryl amine of this invention may be employed in an photoconductive imaging member of this invention. The expression "hydrogen bonding" is defined as an attractive force or bridge occuring between the polar hydroxy containing arylamine and a hydrogen bonding resin in which a hydrogen atom of the polar hydroxy arylamine is attracted to two unshared electrons of a resin containing polarizable groups. The hydrogen atom is the positive end of one polar molecule and forms a linkage with the electronegative end of the other polar molecule. Typical polar resins include polyamides such as the condensation product of adipic acid and hexamethylenediamine and the condensation product of sebacic acid and hexamethylenediamine, polycarbonates, polyesters, polyurethanes, polymethacrylates, maleic anhydride/styrene copolymers, cellulose polymers, and the like. Generally, molecular weights of the polar resin can vary from about 5,000 to about 1,000,000. The materials most preferred as the resin hydrogen bonding material are polyamides with a low molecular weight possessing alcohol solubility (available as Elvamide 8061 and Elvamide 8064 from E.I. DuPont de Nemours Company).

Generally, from about about 10 percent to about 50 percent by weight of the hydroxy arylamine of this invention is combined with from about about 90 percent to about 50 percent by weight of the polar resin to form the hydrogen bonded mixture. The optimum weight percent loading range is dependent on a layers thickness and the loading of other active components e.g. generator pigments. Hence, generator layers typically thin $\leq 2$ micrometers and possessing high loadings of pigment require the lowest content of the hydroxyarylamine compounds, about 5-30 weight percent of the polar resin. Overcoating layers are also typically thin 2 micrometers to 10 micrometers and thus lower hydroxyarylamine loadings may be used. For use in transparent layers which are typically thicker, about 15 micrometers to 25 micrometers, a minimum of 35 weight percent based on the polar resin is desirable. The hydrogen bonded mixture of this invention should be capable of supporting the injection of photogenerated holes from the generation material and capable of allowing the transport of these holes through the active transport layer in order to discharge the surface charge on the active transport layer. Typically, a solvent or mixture of solvents is chosen which dissolves both the polymeric resin and the active small molecules of this invention. Typical solvents include tetrahydrofuran, toluene, methylene chloride, methanol, ethanol and the like. It is known in the scientific literature that hydrogen bonding occurs in the type of resins referred to above. To determine if the interaction is sufficient to prevent leaching, the composition is exposed to a liquid developer ink vehicle, e.g. Isopar L. After a period of time, 24 hours for example, the liquid is examined for the presence of any trace of the active hydroxy arylamine molecule. Typical active hydroxy arylamine small molecules exhibit flourescence upon exposure to ultraviolet light and their presence in the liquid ink vehicle can be determined by detection of this fluoresence with the naked eye.

The photoreceptor substrate may be opaque or substantially transparent and may comprise numerous suitable materials having the required mechanical properties. Accordingly, the substrate may comprise a layer of an electrically non-conductive or conductive material such as an inorganic or an organic composition. As electrically non-conducting materials there may be employed various resins known for this purpose including polyesters, polycarbonates, polyamides, polyurethanes, and the like. The electrically insulating or conductive substrate may be rigid or flexible and may have any number of different configurations such as, for example, a cylinder, sheet, a scroll, an endless flexible belt, and the like. Preferably, the substrate is in the form of an endless flexible belt and comprises a commercially available biaxially oriented polyester known as Mylar, available from E.I. du Pont de Nemours & Co. or Melinex available from ICI.

The thickness of the substrate layer depends on numerous factors including economical considerations. Thus, the substrate layer for a flexible belt may be of substantial thickness, for example, over 200 micrometers, or of minimum thickness less than 50 micrometers, provided there are no adverse effects on the final photoconductive device. In one flexible belt embodiment, the thickness of this layer ranges from about 65 micrometers to about 150 micrometers, and preferably from about 75 micrometers to about 125 micrometers for optimum flexibility and minimum stretch when cycled around small diameter rollers, e.g. 12 millimeter diameter rollers. The surface of the substrate layer is preferably cleaned prior to coating to promote greater adhesion of the deposited coating. Cleaning may be effected by exposing the surface of the substrate layer to plasma discharge, ion bombardment and the like.

The conductive layer may vary in thickness over substantially wide ranges depending on the optical transparency and flexibility desired for the electrophotoconductive member. Accordingly, when a flexible photoresponsive imaging device is desired, the thickness of the conductive layer may be between about 20 angstrom units to about 750 angstrom units, and more preferably from about 50 Angstrom units to about 200 anstrom units for an optimum combination of electrical conductivity, flexibility and light transmission. The conductive layer may be an electrically conductive metal layer and may be formed, for example, on the substrate by any suitable coating technique, such as a vacuum depositing technique. Typical metals include aluminum, zirconium, niobium, tantalum, vanadium and hafnium, titanium, nickel, stainless steel, chromium, tungsten, molybdenum, and the like. If desired, an alloy of suitable metals may be deposited. Typical metal alloys may contain two or more metals such as zirconium, niobium, tantalum, vanadium and hafnium, titanium, nickel, stainless steel, chromium, tungsten, molybdenum, and the like, and mixtures thereof. Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive indium tin oxide as a transparent layer for light having a wavelength between about 4000 Angstroms and about 7000 Angstroms or a conductive carbon black dispersed in a plastic binder as an opaque conductive layer.

After deposition of the metal layer, a hole blocking layer may be applied thereto. Generally, electron blocking layers for positively charged photoreceptors allow holes from the imaging surface of the photoreceptor to migrate toward the conductive layer. Any suitable blocking layer capable of forming an electronic barrier to holes between the adjacent photoconductive layer and the underlying conductive layer may be utilized. The blocking layer may be organic or inorganic and may be deposited by any suitable technique. For example, if the blocking layer is soluble in a solvent, it may be applied as a solution and the solvent can subsequently be removed by any conventional method such as by drying. Typical blocking layers include polyvinylbutyral, organosilanes, epoxy resins, polyesters, polyamides, polyurethanes, pyroxyline vinylidene chloride resin, silicone resins, fluorocarbon resins and the like containing an organo metallic salt. Other blocking layer materials include nitrogen containing siloxanes or nitrogen containing titanium compounds such as trimethoxysilyl propylene diamine, hydrolyzed trimethoxysilyl propyl ethylene diamine, N beta-(aminoethyl) gamma-aminopropyl trimethoxy silane, isopropyl 4-aminobenzene sulfonyl, di(dodecylbenzene sulfonyl) titanate, isopropyl di(4-aminobenzoyl) isostearoyl titanate, isopropyl tri(N-ethylamino-ethylamino) titanate, isopropyl trianthranil titanate, isopropyl tri(N,N-dimethylethylamino) titanate, titanium-4-amino benzene sulfonat oxyacetate, titanium 4-aminobenzoate isostearate oxyacetate, $[H_2N(CH_2)_4]CH_3Si(OCH_3)_2$, (gamma-aminobutyl) methyl diethoxysilane, and $[H_2N(CH_2)_3]CH_3Si(OCH_3)_2$ (gamma-aminopropyl) methyl diethoxysilane, as disclosed in U.S. Pat. Nos. 4,291,110, 4,338,387, 4,286,033 and 4,291,110. The disclosures of U.S. Pat. Nos. 4,338,387, 4,286,033 and 4,291,110 are incorporated herein in their entirety. A preferred blocking layer comprises a reaction product between a hydrolyzed silane and the oxidized surface of a metal ground plane layer. The oxidized surface inherently forms on the outer surface of most metal ground plane layers when exposed to air after deposition. This combination enhances electrical stability at low RH. The hydrolyzed silane has the general formula:

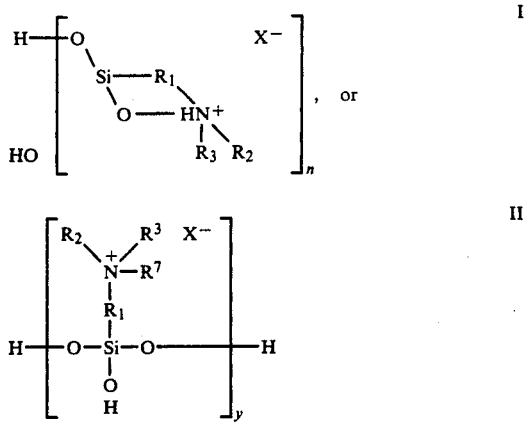

or mixtures thereof, wherein $R_1$ is an alkylidene group containing 1 to 20 carbon atoms, $R_2$, $R_3$ and $R_7$ are independently selected from the group consisting of H, a lower alkyl group containing 1 to 3 carbon atoms and a phenyl group, X is an anion of an acid or acidic salt, n is 1, 2, 3 or 4, and y is 1, 2, 3 or 4.

The imaging member is preferably prepared by depositing on the metal oxide layer of a metal conductive anode layer, a coating of an aqueous solution of the hydrolyzed aminosilane at a pH between about 4 and about 10, drying the reaction product layer to form a siloxane film and applying an adhesive layer of this invention, and thereafter applying electrically operative layers, such as a photogenerator layer and a hole transport layer, to the siloxane film.

The blocking layer should be continuous and have a thickness of less than about 0.5 micrometer because greater thicknesses may lead to undesirably high residual voltage. A blocking layer of between about 0.005 micrometer and about 0.3 micrometer (50 Angstroms-3000 Angstroms) is preferred because charge neutralization after the exposure step is facilitated and optimum electrical performance is achieved. A thickness of between about 0.03 micrometer and about 0.06 micrometer is preferred for metal oxide layers for optimum electrical behavior. Optimum results are achieved with a siloxane blocking layer. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layers are preferably applied in the form of a dilute solution, with the solvent being removed after deposition of the coating by conventional techniques such as by vacuum, heating and the like. Generally, a weight ratio of blocking layer material and solvent of between about 0.05:100 and about 0.5:100 is satisfactory for spray coating. This siloxane coating is described in U.S. Pat. No. 4,464,450 to L. A. Teuscher, the disclosure of this patent being incorporated herein in its entirety.

If desired, a suitable adhesive layer may be applied to the hole blocking layer. Typical adhesive layers include a polyester resin such as Vitel PE-100, Vitel PE-200, Vitel PE-200D, and Vitel PE-222 (all available from Goodyear Tire and Rubber Co.), polyvinyl butyral, and the like.

When an adhesive layer is employed, it should be continuous and preferably, has a dry thickness between about 200 micrometers and about 900 micrometers and more preferably between about 400 micrometers and about 700 micrometers. Any suitable solvent or solvent mixtures may be employed to form a coating solution of the adhesive layer material. Typical solvents include tetrahydrofuran, toluene, methylene chloride, cyclohexanone, and the like, and mixtures thereof. Generally, to achieve a continuous adhesive layer thickness of about 900 angstroms or less by gravure coating techniques, the solids concentration are between about 2 percent and about 5 percent by weight based on the total weight of the coating mixture of resin and solvent. However, any other suitable and conventional technique may be utilized to mix and thereafter apply the adhesive layer coating mixture to the charge blocking layer. Typical application techniques include spraying, dip coating, roll coating, wire wound rod coating, and the like. Drying of the deposited coating may be effected by any suitable conventional technique such as oven drying, infra red radiation drying, air drying and the like.

Any suitable photogenerating layer may be applied to the blocking layer or intermediate layer, if an intermediate layer is employed. In one embodiment, the photogenerating layer may be used in a photoreceptor alone without a separate charge transport layer or, in another embodiment, the photogenerator layer can be utilized with a contiguous hole transport layer as described. If the photogenerating layer is employed without a separate charge transport and is not overcoated with an overcoating layer containing the hydroxy arylamine charge transport material of this invention, the photogenerating layer must comprise photoconductive particles dispersed in a film forming binder comprising the hydroxy arylamine charge transport material of this invention. Typical photoconductive particles for photogenerating binder layers include inorganic photoconductive particles such as amorphous selenium, trigonal selenium, and selenium alloys selected from the group consisting of selenium-tellurium, selenium-tellurium-arsenic, selenium arsenide and mixtures thereof, and organic photoconductive particles including various phthalocyanine pigment such as the X-form of metal free phthalocyanine described in U.S. Pat. No. 3,357,989, metal phthalocyanines such as vanadyl phthalocyanine and copper phthalocyanine, quinacridones available from DuPont under the tradename Monastral Red, Monastral violet and Monastral Red Y, Vat orange 1 and Vat orange 3 trade names for dibromo anthanthrone pigments, benzimidazole perylene, substituted 2,4-diamino-triazines disclosed in U.S. Pat. No. 3,442,781, polynuclear aromatic quinones available from Allied Chemical Corporation under the tradename Indofast Double Scarlet, Indofast Violet Lake B, Indofast Brilliant Scarlet and Indofast Orange, and the like dispersed in a film forming polymeric binder. Selenium, selenium alloy, benzimidazole perylene, and the like and mixtures thereof may be formed as a continuous, homogeneous photogenerating layer. Benzimidazole perylene compositions are well known and described, for example, in U.S. Pat. No. 4,587,189, the entire disclosure thereof being incorporated herein by reference. Multi-photogenerating layer compositions may be utilized where a photoconductive layer enhances or reduces the properties of the photogenerating layer. Examples of this type of configuration are described in U.S. Pat. No. 4,415,639, the entire disclosure of this patent being incorporated herein by reference. Other suitable photogenerating materials known in the art may also be utilized, if desired. A charge generating binder layer comprising particles or layers comprising a photoconductive material such as vanadyl phthalocyanine, metal free phthalocyanine, benzimidazole perylene, amorphous selenium, trigonal selenium, selenium alloys such as selenium-tellurium, selenium-tellurium-arsenic, selenium arsenide, and the like and mixtures thereof are especially preferred because of their sensitivity to white light. Vanadyl phthalocyanine, metal free phthalocyanine and tellurium alloys are also preferred because these materials provide the additional benefit of being sensitive to infra-red light.

Numerous inactive resin materials may be employed in the photogenerating binder layer including those described, for example, in U.S. Pat. No. 3,121,006, the entire disclosure of which is incorporated herein by reference. Typical organic resinous binders include thermoplastic and thermosetting resins such as polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl acetate, polysiloxanes, polyacrylates, polyvinyl acetals, polyamides, polyimides, amino resins, phenylene oxide resins, terephthalic acid resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, and the like. These polymers may be block, random or alternating copolymers.

In the generator layer it is an important function to allow rapid separation of the hole-electron pair generated during the generator's exposure to actinic radiation. For this reason, generator layers which utilize binders incorporate materials capable of transporting one of the charges to the next layer of the imaging device. This can be accomplished by doping a quantity of the hole transporting small molecule used in the transport layer, for example, N,N'-diphenyl-N,N'-bis(3-methylphenyl)-[1,1'-biphenyl]-4,4'-diamine. It is expected that replacement of currently used resin/activating small molecule compositions with the active hydroxy arylamine compounds of this invention will yield generator layers of increased mechanical strength. In addition, by selecting from the broader range of binders compatible with the active molecules of this invention adhesion of the generator layer to layers adjacent to it will be improved.

The hydroxy arylamine of this invention may be added to any suitable inactive polar resin material employed in a generator binder layer. No hydroxy arylamine need be added to the generator layer if another layer in the photoreceptor, such as a charge transport layer or an overcoating layer contains the hydroxy arylamine of this invention. Generally, to gain the benefit of the improved resistance to leaching, cracking, and crazing provided by the hydroxy arylamine of this invention, the outermost layer exposed to liquid developer, be it the photogenerator layer, charge transport layer or overcoating layer, preferably contains a film forming polar resin and an amount of the hydroxy arylamine compound of this invention necessary for the xerographic functioning of the various layers. The optimum weight percent loading range is dependent on the layers thickness and other active components within a specific layer, e.g. generator pigments. Generator layers are generally thin about $\leq 2$ micrometers and can have high loadings of pigments. This lowers the requirement for the amount of hydroxyarylamine compound to be placed in the generator layer, typically about 5–30 weight percent of the polar resin.

For binder layers, the photogenerating composition or pigment is present in the resinous binder composition in various amounts, generally, however, from about 5 percent by volume to about 90 percent by volume of the photogenerating pigment is dispersed in about 10 percent by volume to about 95 percent by volume of the resinous binder, and preferably from about 20 percent by volume to about 30 percent by volume of the photogenerating pigment is dispersed in about 70 percent by volume to about 80 percent by volume of the resinous binder composition. In one embodiment about 8 percent by volume of the photogenerating pigment is dispersed in about 92 percent by volume of the resinous binder composition.

For embodiments in which the photogenerating layers do not contain a resinous binder, the photogenerating layer may comprise any suitable, well known homogeneous photogenerating material. Typical homogeneous photogenerating materials include inorganic photoconductive compounds such as amorphous selenium, selenium alloys selected such as selenium-tellurium, selenium-tellurium-arsenic, and selenium arsenide and organic materials such as chlorindium phthalocyanine, chloraluminum phthalocyanine, vanadyl phthalocyanine, and the like.

The photogenerating layer containing photoconductive compositions and/or pigments and the resinous binder material generally ranges in thickness of from about 0.1 micrometer to about 5.0 micrometers, and preferably has a thickness of from about 0.3 micrometer to about 3 micrometers. The photogenerating binder layer thickness is related to binder content. Higher binder content compositions generally require thicker layers for photogeneration. Thicknesses outside these ranges can be selected providing the objectives of the present invention are met.

Any active charge transport layer employed must be capable of supporting the injection of photo-generated holes from the charge generation layer and allowing the transport of these holes through the transport layer to selectively discharge the surface charge. When the photogenerating layer is sandwiched between the conductive layer and the active charge transport layer, the transport layer not only serves to transport holes, but also protects the photoconductive layer from abrasion or chemical attack and therefore extends the operating life of the electrophotographic imaging member. The charge transport layer should exhibit negligible, if any, discharge when exposed to a wavelength of light useful in xerography, e.g. 4000 angstroms to 9000 angstroms. Therefore, the charge transport layer is substantially transparent to radiation in a region in which the photoconductor is to be used. Thus, the active charge transport layer is a substantially non-photoconductive material which supports the injection of photogenerated holes from the generation layer. The active transport layer is normally transparent when exposure is effected through the active layer to ensure that most of the incident radiation is utilized by the underlying charge carrier generator layer for efficient photogeneration. When used with a transparent substrate, imagewise exposure may be accomplished through the substrate with all light passing through the substrate. In this case, the active transport material need not be transmitting in the wavelength region of use. The charge transport layer in conjunction with the generation layer in the instant invention is a material which is an insulator to the extent that an electrostatic charge placed on the transport layer is not conducted in the absence of illumination.

If a charge transport layer is employed as an outer layer of a photoreceptor, it is preferred that the transport layer consist essentially of the active materials of this invention described above comprising a hydroxy arylamine hydrogen bonded to a polar resin, particularly when the photoreceptor is to be developed with liquid inks.

The active charge transport layer should be capable of supporting the injection of photogenerated holes from the generation material and capable of allowing the transport of these holes through the active transport layer in order to discharge the surface charge on the active transport layer. The substituents should be free from electron withdrawing groups such as $NO_2$ groups, CN groups, and the like.

Any suitable solvent may be employed to apply the transport layer material to the underlying layer. Typical solvents include tetrahydrofuran, toluene, methylene chloride, various mixtures thereof, and the like. Methylene chloride solvent is a particularly desirable component of the charge transport layer coating mixture for adequate dissolving of all the components and for its low boiling point.

Any suitable and conventional technique may be utilized to mix and thereafter apply the charge transport layer coating mixture to the underlying surface, e.g. charge generating layer. Typical application techniques include spraying, dip coating, roll coating, wire wound rod coating, and the like. Drying of the deposited coating may be effected by any suitable conventional technique such as oven drying, infra red radiation drying, air drying and the like.

Generally, the thickness of the hole transport layer is between about 5 to about 100 micrometers, but thicknesses outside this range can also be used. The hole transport layer should be an insulator to the extent that the electrostatic charge placed on the hole transport layer is not conducted in the absence of illumination at a rate sufficient to prevent formation and retention of an electrostatic latent image thereon. In general, the ratio of the thickness of the hole transport layer to the charge generator layer is preferably maintained from about 2:1 to 200:1 and in some instances as great as 400:1.

An especially preferred transport layer employed in one of the two electrically operative layers in a multilayered photoconductor of this invention comprises from about 30 percent to about 50 percent by weight of N,N'-diphenyl-N,N'-bis(3-hydroxyphenyl)-[1,1'-biphenyl]-4,4'-diamine and from about 70 percent to about 50 percent by weight of hydroxypropyl cellulose. This yields a transport layer resistant to surface crystallization of the active molecule.

The active, hole transporting hydroxy arylamine materials of this invention are capable of hydrogen bonding with polar resins. This can lead to improved compatibility with resins currently found unsuitable due to small molecule incompatibility, phase separation. The active small molecule N,N'-diphenyl-N,N'-bis(3-methylphenyl)-[1,1'-biphenyl]-4,4'-diamine is compatible in "phenoxy resin" only to the extent of several (2-3) weight percent. The active molecules of this invention are compatible with "phenoxy resin" at 50 weight percent loadings. A common occurrance seen with N,N'-diphenyl-N,N'-bis(3-methylphenyl)-[1,1'-biphenyl]-4,4'-diamine/polycarbonate 50 weight percent loadings transport layers is the surface crystallization caused by handling, i.e. fingerprints. A transport layer composed of N,N'-diphenyl-N,N'-bis(3-hydroxyphenyl)-[1,1'-biphenyl]-4,4'-diamine 50 parts and phenoxy resin (PKHH phenoxy resin from Union Carbide Corp.) 50 parts shows no evidence of surface crystallization when subjected to repeated handling.

An overcoating layer may be applied to the outermost surface of the multilayered electrophotographic imaging member of this invention. This overcoating layer must be used if neither the generator layer nor the transport layer contains the hydroxy arylamine compound of this invention hydrogen bonded to a polar resin. If neither the generator layer nor the transport layer contains the hydroxy arylamine compound of this invention hydrogen bonded to a polar resin, the overcoating layer must be electrically active and contain the hydroxy arylamine compound of this invention hydrogen bonded to a polar resin to support the injection of photo-generated holes and electrons from the photogenerator layer and allow the transport of these holes or electrons through the organic layer to selectively discharge the surface charge. The active overcoating layer not only serves to transport holes, but also protects the underlying layer from abrasion or chemical attack and therefore extends the operating life of the electrophotographic imaging member, particularly in liquid development systems. The active overcoating layer should exhibit negligible, if any, discharge when exposed to a wavelength of light useful in xerography, e.g. 4000 angstroms to 9000 angstroms. Therefore, the active overcoating layer is substantially transparent to radiation in a region in which the photoconductor is to be used. Thus, the active overcoating layer is a substantially non-photoconductive material which supports the injection of photogenerated holes from the generation layer. The active overcoating layer is normally transparent when exposure is effected through the active layer to ensure that most of the incident radiation is utilized by the underlying charge carrier generator layer for efficient photogeneration. When used with a transparent substrate, imagewise exposure may be accomplished through the substrate with all light passing through the substrate. In this case, the active overcoating material need not be transmitting in the wavelength region of use. The active overcoating layer in conjunction with the generation layer in the instant invention is a material which is an insulator to the extent that an electrostatic charge placed on the overcoating layer is not conducted in the absence of illumination.

Part or all of the active resin materials to be employed in the overcoating layer may be replaced by the active hydrogen bonded materials of this invention described above comprising a hydroxy arylamine hydrogen bonded to a polar resin. The ratio of small molecule hydroxy arylamine to polar polymer matrix can range from about 5:95 to about 70:30. Optimum electrical and mechanical perfomance are obtained with a ratio of small molecule hydroxy arylamine to polar polymer matrix range from about 5:95 to about 30:70 by weight.

The active charge overcoating layer should be capable of supporting the injection of photogenerated holes from the generation material and capable of allowing the transport of these holes through the active overcoating layer in order to discharge the surface charge on the active overcoating layer.

Any suitable solvent may be employed to apply the overcoating layer material to the underlying layer. Typical solvents include alcohols, ketones, tetrahydrofuran, and the like. An alcohol solvent is a particularly desirable component of the overcoating layer coating mixture particularly where the underlying layer comprises solvent sensitive components.

An especially preferred active overcoating layer employed on photoconductors of this invention comprises from about 10 percent to about 40 percent by weight of N,N,N',N'-tetra(m-hydroxyphenyl)[1,1'-biphenyl]-4,4'-diamine and from about 60 percent to about 50 percent by weight of alcohol soluble polyamide resin.

Any suitable and conventional technique may be utilized to mix and thereafter apply the charge overcoating layer coating mixture to the underlying surface, e.g. charge transport layer. Typical application techniques include spraying, dip coating, roll coating, wire wound rod coating, and the like. Drying of the deposited coating may be effected by any suitable conventional technique such as oven drying, infra red radiation drying, air drying and the like.

Generally, the thickness of the overcoating layer is between about 2 to about 10 micrometers, but thicknesses outside this range can also be used.

Other layers such as conventional ground strips comprising, for example, conductive particles dispersed in a film forming binder may be applied to one edge of the photoreceptor in contact with the conductive surface, blocking layer, adhesive layer or charge generating layer.

Optionally, a back coating may be applied to the side opposite the photoreceptor to provide flatness and/or abrasion resistance. The backcoating layers may comprise organic polymers or inorganic polymers that are electrically insulating or slightly semi-conductive.

The electrophotographic member of the present invention containing the hydrogen bonded hydroxy arylamine and polar resin in at least the generator, transport or overcoating layer may be employed in any suitable and conventional electrophotographic imaging process which utilizes charging prior to imagewise exposure to activating electromagnetic radiation. Conventional positive or reversal development techniques may be employed to form a marking material image on the imaging surface of the electrophotographic imaging member of this invention. Thus, by applying a suitable electrical bias and selecting toner having the appropriate polarity of electrical charge, one may form a toner image in the negatively charged areas or discharged areas on the imaging surface of the electrophotographic member of the present invention. More specifically, for positive development, charged toner particles of one polarity are attracted to the oppositely charged electrostatic areas of the imaging surface and for reversal development, charged toner particles are attracted to the discharged areas of the imaging surface. Where the transport layer of this invention is sandwiched between a photogenerating layer and a conductive surface, a positive polarity charge is normally applied prior to imagewise exposure to activating electromagnetic radiation. Where the photogenerating layer layer of this invention is sandwiched between a transport layer and a conductive surface, a negatie polarity charge is normally applied prior to imagewise exposure to activating electromagnetic radiation.

The electrophotographic member of the present invention exhibits greater resistance to cracking, crazing, crystallization of arylamine compounds, phase separation of arylamine compounds and leaching of arylamine compounds during cycling.

The invention will now be described in detail with respect to the specific preferred embodiments thereof, it being understood that these examples are intended to be illustrative only and that the invention is not intended to be limited to the materials, conditions, process parameters and the like recited herein. All parts and percentages are by weight unless otherwise indicated.

EXAMPLE 1

Following the procedure of Example 1 in U.S. Pat. No. 4,588,666, N,N'-di(3-methoxyphenyl)-N,N'-diphenyl-[1,1-biphenyl]-4,4' diamine was synthesized from m-iodoanisole to achieve a yield of 90 percent, m.p. 120°-125° C. N,N'-diphenyl-N,N'-bis(3-hydroxyphenyl)-[1,1'-biphenyl]-4,4'-diamine was prepared, for example, from the N,N'-di(3-methoxyphenyl)-N,N'-diphenyl-[1,1-biphenyl]-4,4'diamine by placing into a two liter three-necked round bottom flask, equipped with a mechanical stirrer and an argon gas inlet, 137.5 gms N,N'-diphenyl-N,N'-bis(3-methoxyphenyl)-[1,1'-biphenyl]-4,4'diamine (0.25 moles), 223.5 gms anhydrous sodium iodide (1.5 moles) and 500 millilters warm sulfolane (distilled). The contents of the flask were heated to 120° C. then cooled to 60° C. Five milliliters of D.I. water was added dropwise, followed by 190.5 milliliters of trimethylchlorosilane (1.5 moles)). The contents were allowed to heat at 60°-75° C. for six hours. HPLC analysis was utilized to determine when the reaction was complete. The contents of the flask were poured into a 3 liter Erlenmeyer flask containing 1.5 liter of deionized water. The water layer was decanted and the dark oily residue taken up into 500 milliliters methanol. The methanol solution was extracted with two 400 milliliter portions of hexane to remove the hexamethyldisiloxane by-products. The methanol solution was roto-evaported to remove the solvents. The residue was taken up into 500 milliliters of acetone and then precipitated into 1.5 liters deionized water. The off-white solid was filtered and then washed with deionized water and dried in vacuo. The crude N,N'-diphenyl-N,N'-bis(3-hydroxyphenyl)-[1,1'-biphenyl]-4,4'-diamine was placed into a two liter round-bottom flask containing a magnetic stirrer and one liter toluene. Fifty gms. Florisil® (Florisil is a registered trademark of Floridin Co.) was added to the flask and allowed to stir for two hours. The dark Florisil® was filtered off, leaving a pale yellow toluene solution. The toluene was roto-evaporated to yield a pale yellow viscous oil. The oily product was dissolved in 400 milliliters acetone then diluted with 400 milliliters heptane and allowed to crystallize. The colorless crystals were filtered. Additional product was obtained by roto-evaporating the acetone from the filtrate. Yield was 85 percent, m.p. 113°-17° C.

EXAMPLE II

A N,N-bis(3-methoxy phenyl)amine precursor for N,N,N'N'-tetra(m-methoxy-phenyl)-[1,1'-biphenyl]-4,4'-diamine was prepared by placing into a two liter three-necked round bottom flask, equipped with a mechanical stirrer and an argon inlet 166 gms m-methoxy acetanilide (1 mole, 66 gms copper bronze, 300 gms m-iodoanisole (1.3 moles Aldrich Chem. Co.) and 276 gms anhydrous potassium carbonate (2 moles). The reaction mixture was heated with stirring to 190° C. A Dean-Stark trap was used to collect the water of reaction. After 24 hours the reaction was cooled, then diluted with 800 milliliters 2-propanol. The mixture was heated to reflux, then filtered hot. To the filtrate was added a solution of 102 gms. potassium hydroxide in 89 milliliters deionized water and the flask was heated to reflux. After three hours, the mixture was diluted with an equal volume of water and allowed to settle. The water layer was decanted off leaving a dark oil. The dark oil was taken up into one liter of toluene and dried with anhydrous magnesium sulfate. Following filtration, the toluene solution was roto-evaporated to remove the toluene. Distillation of the dark residue at 175° with 6 mm Hg yielded a pale yellow oil. Yield of the isomeric mixture was 140 gms. This isomeric mixture included predominately N,N'-bis(3-methoxyphenyl)amine.

EXAMPLE III

N,N,N',N'-tetra(m-hydroxy phenyl)-[1,1'-biphenyl]-4,4'-diamine was prepared, for example, by placing into a two liter three-necked round bottom flask, equipped with a mechanical stirrer and an argon inlet 75.9 gms of an isomeric mixture of N,N-bis(methoxy phenyl)amine (0.33 moles), 44.4 gms diiodobisphenyl (0.11 moles), 50 gms copper bronze, 150 milliliters ISOPAR L (Exxon Chem) and 89 gms anhydrous potassium carbonate. The reaction mixture was heated with stirring to 200° C. A Dean-Stark trap was used to collect the water formed during the reaction. After 24 hours, the reaction was allowed to cool and 400 milliliters of toluene was added. The mixture was heated to reflux temperature and filtered hot. The reddish solution was roto-evaporated to remove toluene. The Isopar L ® was decanted off the viscous precipitate. The dark oil was dissolved in 400 milliliters of toluene and the solution was stirred with 50 gms Florisil ® for two hours. The solution was filtered to remove the dark Florisil ® yielding a pale yellow solution. The solution was roto-evaporated to remove the toluene. The yellow oil was dissolved in 200 milliliters of acetone and diluted with 200 milliliters of n-heptane and allowed to crystallize. Filtration yielded an off-white solid, yield 30 gms.

EXAMPLE IV

N,N,N',N'-tetra(m-hydroxyphenyl)-[1,1'-biphenyl]-4,4'-diamine was prepared, for example, by placing into a one liter three-necked round bottom flask equipped with a mechanical stirrer and an argon inlet 30 gms N,N,N'N'-tetra(m-methoxyphenyl)-[1,1'-biphenyl]-4,4'-diamine (0.05 mole), 90 gms anhydrous sodium iodide (0.6 mole) and 200 milliliters warm sulfolane (distilled). The contents of the flask were heated to 120° C. then cooled to 60° C. Two milliliters deionized water was added dropwise followed by 76 milliliters trimethylchlorosilane (0.6 moles). The contents were allowed to heat at 60°-75° C. for six hours. HPLC analysis was utilized to determine when the reaction was complete. The contents of the flask were poured into a two-liter Erlenmeyer flask containing one liter of D.I. water. The water layer was decanted and the dark oily residue taken up into 300 milliliters of methanol. The methanol solution was extracted with two-300 milliliter portions of hexane to remove the hexamethyldisiloxane by-products. The methanol solution was roto-evaporated to remove the solvents. The residue was taken up into 200 milliliters of acetone and then precipitated into one liter of deionized water. The dark oily product was dissolved in 300 milliliters of diisopropylether and dried with anhydrous magnesium sulfate. The waterfree solution was combined with 50 gms of Florisil ® and stirred for two hours. The diisopropyl ether was removed using a roto-evaporator. The yellow oily residue was dissolved in 100 milliliters of acetone and diluted with 200 milliliters of heptane. The flask was allowed to set overnight at $-5°$ C. The off-white solid was filtered off and dried. Yield was 16 gms. (60 percent).

EXAMPLE V

A control experiment was conducted with a multilayer electrophotographic imaging member comprising an aluminized Mylar substrate having a thickness of about 5 mils, coated with a generating layer of trigonal selenium dispersed in polyvinyl carbazole, having a thickness of about 2 micrometers, overcoated with a transport layer of N,N'-diphenyl-N-N'-bis(3-methyl phenyl)[1,1'biphenyl]-4,4'-diamine dispersed in poly carbonate resin having a thickness of about 21 microns. This imaging member sample was bent over a 3" roller and exposed to Isopar-L ink solvent. Leaching of the N,N'-diphenyl-N-N'-bis(3-methylphenyl)[1,1'biphenyl]-4,4'-diamine small molecules and cracking of the transport layer was observed in as little as 1 hour and severe degradation of the sample was evident in 24 hours.

EXAMPLE VI

A control experiment was conducted with a multilayer electrophotographic imaging member comprising an aluminized Mylar substrate having a thickness of about 5 mils, coated with a generating layer of trigonal selenium dispersed in polyvinyl carbazole, having a thickness of about 2 micrometers, overcoated with a transport layer of N,N'-diphenyl-N-N'-bis(4-hydroxyphenyl)[1,1'-biphenyl]-4,4'-diamine dispersed in polycarbonate resin having a thickness of about 21 microns. Flat plate electrical scanning of this sample showed a $V_o$ (charge acceptance) of $-820$ V. Despite repeated exposure to light of the scanner, the imaging member failed to discharge.

EXAMPLE VII

An electrophotographic imaging member having the structure described in Example 1 was overcoated with a methyl alcohol solution of N,N,N'N'-tetra(m-hydroxyphenyl)-[1,1'-biphenyl]-4,4'-diamine and polyamide resin (Elvamide 8061 availble from E. I. duPont deNemours & Co.) (50 of the parts hydroxyarylamine/50 parts Elvamide) using a Mayer coating rod to obtain a dry film thickness of about 4.0 micrometers after oven drying at 85° C. for 30 minutes. Flat plate electrical scanning of this sample showed a $V_o$ (charge acceptance) of $-820$ V and a $V_R$ (residual voltage) of $-15$ V. after 10 consecutive cycles. Exposure of the electrophotographic imaging member to Isopar Link solvent while bent over a 3" roll for 6 days showed no small molecule leaching and no film cracking.

EXAMPLE VIII

An electrophotographic imaging member having the structure described in Example was overcoated with an ethyl alcohol solution of N,N'-(bis(3methoxyphenyl) amine and polyamide resin (Elvamide 8061 available from E. I. duPont deNemours & Co.) (50 parts of the hydroxyarylamine/50 parts Elvamide) using a Mayer coating rod to obtain a dry film thickness of about 6.0 microns after oven drying at 85° C. for 30 minutes. Flat plate electrical scanning of this sample showed a $V_o$ of $-920$ V and a $V_R$ of $-20$ V after 10 consecutive cycles. Exposure of the electrophotographic imaging member to Isopar Link solvent while bent over a 3" roll for 2 days showed only a trace of small molecule leaching and no film cracking.

EXAMPLE IX

An imaging member as described in Example 1 was overcoated with (50/50 percent by volume mixture of acetone/methyl ethyl ketone solution of polyurethane resin (Estar 5720, available from Goodyear Chemical Co.) and N,N,N'N'-tetra(m-hydroxyphenyl)-[1,1'-biphenyl]-4,4'-diamine (50 parts of the hydroxyarylamine/50 parts Estar 5720) using a Mayer coating rod to obtain a dry film thickness of about 8.0 micrometers after oven drying for 30 minutes at 85° C. Flat plate electrical scanning of this sample showed a $V_o$ of $-860$ V and a $V_R$ of $-20$ V after 10 consecutive cycles. Exposure of the electrophotographic imaging member to Isopar L ink solvent for 2 days showed only a trace of small molecule leaching and no film cracking.

EXAMPLE X

An imaging member as described in Example 1 was overcoated with a 70/30 percent by volume mixture of n-proponol/1,1,2-trichloroethane solution of polyamide resin (Elvamide 8064, available from E. I. duPont de Nemours Co.) and N,N,N'N'-tetra(m-hydroxyphenyl)-[1,1'-biphenyl]-4,4'-diamine (50 parts of the hydroxyarylamine/50 parts Elvamide 8064) using a Mayer rod to obtain a dry film thickness of about 6.0 micrometers after oven drying at 85° C. for 30 minutes. Flat plate electrical scanning of this sample showed a $V_o$ of $-800$ V and $V_R$ of $-10$ V after 10 consecutive cycles. Exposure of the electrophotographic imaging member to Isopar Link solvent while bent over a 3" roll for 4 days showed no small molecule leaching and no film cracking.

EXAMPLE XI

An imaging member as described in Example 1 was overcoated with a tetrahydrofuran solution of styrene-ethylacrylate copolymer resin (1512 available from Monsanto) and N,N,N'N'-tetra(m-hydroxyphenyl)-[1,1'-biphenyl]-4,4'-diamine (50 ml parts of the hydroxyarylamine/50 parts 1512 resin) using a spray gun device to obtain a dry film thickness of about 6.0 micrometers after drying 30°/85° C. Both flat plate electrical and Isopar L exposure tests showed comparable results to those obtained in the above cited examples.

EXAMPLE XII

An imaging member was overcoated as described in Example II and was placed into a Savin 5040 xerographic liquid toner machine using negative charging.

A total of 21,000 acceptable prints over a period of 4 weeks were obtained at which time the experiment was terminated.

EXAMPLE XIII

On an aluminum plate on which was deposited .5 micrometers of amorphous selenium was coated a tetrahydrofuran solution of polyester (Vitel PE-100 available from Goodyear Tire & Rubber Company) and N,N'-diphenyl-N,N'-bis(3-hydroxy-phenyl)-[1,1'-biphenyl]-4,4'diamine (50 parts hydroxyarylamine/50 parts Vitel PE-100) micrometer draw bar. An ~12 micrometer dry film was obtained after drying under vacuum for 12 hours. Flat plate electrical scanning of this sample showed a $V_o$ (charge acceptance) of $-600$ V and a $V_R$ (residual voltage) of approximately 0V. Exposure to Isopar L, an isoparaffinic hydrocarbon, for 1 week showed no small molecule leaching and no film cracking.

Although the invention has been described with reference to specific preferred embodiments, it is not intended to be limited thereto, rather those skilled in the art will recognize that variations and modifications may be made therein which are within the spirit of the invention and within the scope of the claims.

We claim:

1. A hydroxy arylamine compound represented by the formula:

$$HO-Ar-N(-Z)_{\overline{\phantom{x}}}\left[\begin{array}{c}N-Ar\\|\\Ar'\end{array}\right]_m-OH$$

wherein:

m is 0 or 1,

Z is selected from the group consisting of:

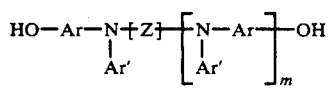

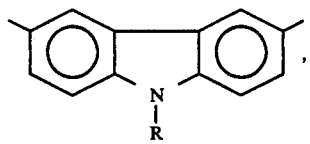

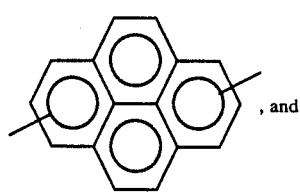

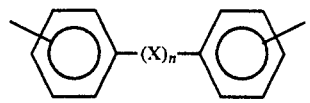

n is 0 or 1,

Ar is selected from the group consisting of:

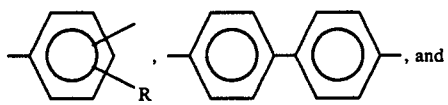

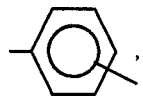

R is selected from the group consisting of —CH$_3$, —C$_2$H$_5$, —C$_3$H$_7$, and —C$_4$H$_9$, Ar' is selected from the group consisting of:

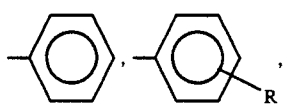

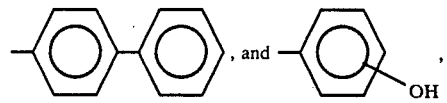

X is selected from the group consisting of:

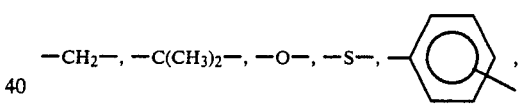

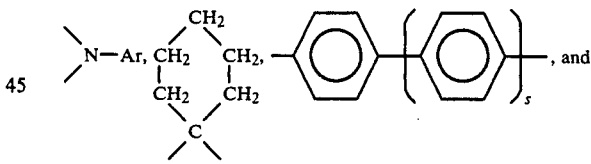

s is 0, 1 or 2, said hydroxy arylamine compound being free of any segment having the formula:

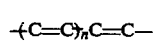

where n=0 or 1, in one or more aromatic rings directly between an —OH group and the nearest nitrogen atom.

2. The hydroxy arylamine compound N,N'-diphenyl-N,N'-bis(3-hydroxyphenyl)-[1,1'-biphenyl]-4,4'-diamine.

3. The hydroxy arylamine compound N,N,N'N'-tetra(m-hydroxyphenyl)-[1,1'-biphenyl]-4,4'-diamine.

* * * * *